US00PP14521P29

(12) United States Plant Patent
van Rijn

(10) Patent No.: US PP14,521 P2
(45) Date of Patent: Feb. 10, 2004

(54) ANTHURIUM PLANT NAMED 'BABY SMILE'

(50) Latin Name: *Anthurium andreanum*
Varietal Denomination: Baby Smile

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 10/368,885

(22) Filed: Feb. 18, 2003

(51) Int. Cl.[7] ..... A01H 5/00
(52) U.S. Cl. ..... Plt./365
(58) Field of Search ..... Plt./365

*Primary Examiner*—Kent Bell
(74) *Attorney, Agent, or Firm*—C. A. Whealy

(57) ABSTRACT

A new and distinct cultivar of Anthurium plant named 'Baby Smile', characterized by its upright and outwardly spreading plant habit; freely clumping growth habit; durable dark green leaves; dark red-colored spathes with white-colored spadices that are positioned above and beyond the foliage on strong and erect scapes; freely flowering habit; and good inflorescence longevity.

2 Drawing Sheets

Botanical classification/cultivar designation: *Anthurium andreanum* cultivar Baby Smile.

BACKGROUND OF THE INVENTION

The present invention relates to a new and distinct cultivar of Anthurium plant, botanically known as *Anthurium andreanum*, and hereinafter referred to by the name 'Baby Smile'.

The new Anthurium is a product of a planned breeding program conducted by the Inventor in Schipluiden, The Netherlands. The objective of the program is to create and develop new compact, freely clumping and freely flowering Anthurium cultivars with strong roots, dark green leaves, attractive spathe color, and good inflorescence longevity.

The new Anthurium originated from a cross by the Inventor on Mar. 7, 1998 of a proprietary selection of *Anthurium andreanum* identified as code number 9515, not patented, as the female, or seed, parent with a proprietary selection of *Anthurium andreanum* identified as code number 9715, not patented, as the male, or pollen, parent. The cultivar Baby Smile was discovered and selected by the Inventor as a plant within the progeny of the stated cross in a controlled environment in Schipluiden, The Netherlands in November, 1999.

Asexual propagation of the new cultivar by meristem culture in a laboratory in Belgium since December, 1999, has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Baby Smile. These characteristics in combination distinguish 'Baby Smile' as a new and distinct cultivar:

1. Upright and outwardly spreading plant habit.
2. Freely clumping growth habit.

3. Durable dark green leaves.
4. Dark red-colored spathes with white-colored spadices that are positioned above and beyond the foliage on strong and erect scapes.
5. Freely flowering habit.
6. Good inflorescence longevity.

Plants of the new Anthurium can be compared to plants of the female parent, the proprietary selection identified as code number 9515. In side-by-side comparisons conducted in Schipluiden, The Netherlands, plants of the new Anthurium differed from plants of the selection 9515 in the following characteristics:

1. Plants of the new Anthurium had darker green-colored leaves than plants of the selection 9515.
2. Plants of the new Anthurium had flatter spathes than plants of the selection 9515.
3. Spathe color of plants of the new Anthurium was dark red whereas spathe color of plants of the selection 9515 was orange.

Plants of the new Anthurium can be compared to plants of the male parent, the proprietary selection identified as code number 9715. In side-by-side comparisons conducted in Schipluiden, The Netherlands, plants of the new Anthurium differed from plants of the selection 9715 in the following characteristics:

1. Plants of the new Anthurium were more compact than plants of the selection 9715.
2. Plants of the new Anthurium were more freely clumping than plants of the selection 9715.
3. Plants of the new Anthurium had dark red-colored spathes whereas plants of the selection 9715 had white-colored spathes with red and green-colored venation.

Plants of the new Anthurium can also be compared to plants of the cultivar Baby Red, disclosed in U.S. Plant Pat. No. 11,468. In side-by-side comparisons conducted in Schipluiden, The Netherlands, plants of the new Anthurium differed from plants of the cultivar Baby Red in the following characteristics:

1. Plants of the new Anthurium were larger than plants of the cultivar Baby Red.
2. Leaves and spathes of plants of the new Anthurium were more rounded than leaves and spathes of plants of the cultivar Baby Red.

3. Plants of the new Anthurium and the cultivar Baby Red differed in spathe coloration.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph on the first sheet comprises a side perspective view of a typical flowering plant of the cultivar Baby Smile.

The photograph on the second sheet comprises a close-up view of a typical inflorescence of 'Baby Smile'.

DETAILED BOTANICAL DESCRIPTION

In the following description, color references are made to The Royal Horticultural Society Colour Chart, 2001 Edition, except where general terms of ordinary dictionary significance are used. The aforementioned photographs and the following observations and measurements describe 10-month old plants grown in 14-cm containers in Schipluiden, The Netherlands, in a glass-covered greenhouse with an average day temperature of 23° C., an average night temperature of 21° C. and light levels about 6 kilolux.

Botanical classification: *Anthurium andreanum* cultivar Baby Smile.

Parentage:

*Female parent.*—Proprietary selection of *Anthurium andreanum* identified as code number 9515, not patented.

*Male parent.*—Proprietary selection of *Anthurium andreanum* identified as code number 9715, not patented.

Propagation:

*Method.*—By meristem culture.

*Time to initiate roots on a meristem-cultured plant.*—About 28 days at 20 to 24° C.

*Time to develop roots on a meristem-cultured plant.*—About 270 days at 20 to 24° C.

*Root description.*—Thick, fleshy, dark pink to cream-colored; lateral roots, abundant.

Plant description:

*Plant shape.*—Upright and outwardly spreading plant habit, inverted triangle, symmetrical.

*Growth habit.*—Freely clumping, bushy and dense growth habit; about nine clumps per plant. Appropriate for 14-cm containers; moderately vigorous.

*Plant height, from soil level to top of leaf plane.*—About 36 cm.

*Plant height, from soil level to top of inflorescences.*—About 45 cm.

*Plant diameter or spread.*—About 40 cm.

*Crop time.*—About 10 months are usually required from planting of young plants to finished plants in a 14-cm container.

*Foliage description.*—Arrangement: Alternate; simple. Quantity per plant: About 45. Length: About 12.5 cm. Width: About 7.6 cm. Shape: Deltoid. Apex: Apiculate. Base: Cordate to truncate. Margin: Entire. Texture, upper and lower surfaces: Leather; glabrous, smooth; durable. Venation pattern: Pinnate. Color: Young leaves, upper surface: More green than 146A. Young leaves, lower surface: 146B. Mature leaves, upper surface: Slightly more green than 147A. Mature leaves, lower surface: 146B. Venation, upper and lower surfaces: 146D. Petiole: Length: About 24.5 cm. Diameter, just below geniculum: About 3.5 mm. Diameter, at plant base: About 4.5 mm. Texture: Smooth. Color: 146B; towards base, 184C. Geniculum length: About 2.1 cm. Geniculum diameter: About 4 mm. Geniculum color: 146A to 146B. Wing length: About 2.8 cm. Wing diameter: About 4.5 mm. Wing color: 184A to 184B.

Inflorescence description:

*Inflorescence arrangement.*—Spathes with spadices held above and beyond the foliage. Flowering structures arise from leaf axils. Freely and continuous flowering during the autumn in Schipluiden, The Netherlands. Typically about seven inflorescences per plant. Inflorescences not fragrant.

*Inflorescence longevity.*—Inflorescences last about two months under winter conditions and about three months under summer conditions; inflorescences persistent.

*Spathe.*—Length: About 3.3 cm. Width: About 7.6 cm. Depth: About 5.1 cm. Shape: Reniform to cordate. Apex: Abruptly acute to mucronulate. Base: Cordate to attenuate. Margin: Entire. Texture, upper and lower surfaces: Leathery; glabrous, smooth. Aspect: Moderately cupped. Color: When opening, front surface: 46A; towards the basal margin, 146A to 146B. When opening, back surface: 53B; towards the basal margin, 146A. Fully developed, front surface: 46A; towards the basal margin, 146A; overall spathe color becoming closer to 53A with development. Fully opened, back surface: 53B; towards the basal margin, 146A to 146B.

*Spadix.*—Length: About 3.2 cm. Diameter: About 6 mm. Shape: Columnar, tapering towards the apex; apex, obtuse. Cross section: Rounded. Aspect: About 10° from vertical. Color: Immature: 16D. Mature: Between 155D and 4D.

*Flowers.*—Quantity per spadix: Numerous, about 150. Shape: Rounded. Height: Less than 0.5 mm. Diameter: About 0.8 mm.

*Reproductive organs.*—Androecium: Anther color: 11D. Amount of pollen: Moderate. Pollen color: 11C. Gynoecium: Stigma shape: Ovoid. Stigma color: N155D. Ovary color: N155D.

*Scape.*—Length: About 30.4 cm. Diameter: About 3 mm. Strength: Strong. Aspect: Erect to slightly outwardly slanted, about 20° from vertical. Color: 144A; towards the spathe, 146B.

*Seed and fruit.*—Seed and fruit development has not been observed on plants of the new Anthurium.

Disease/pest resistance: Under commercial production conditions, plants of the new Anthurium have not been observed to be resistant to pathogens or pests common to Anthurium.

Temperature tolerance: Plants of the new Anthurium have been observed to tolerate temperatures from 14 to 35° C.

It is claimed:

1. A new and distinct cultivar of Anthurium plant named 'Baby Smile', as illustrated and described.

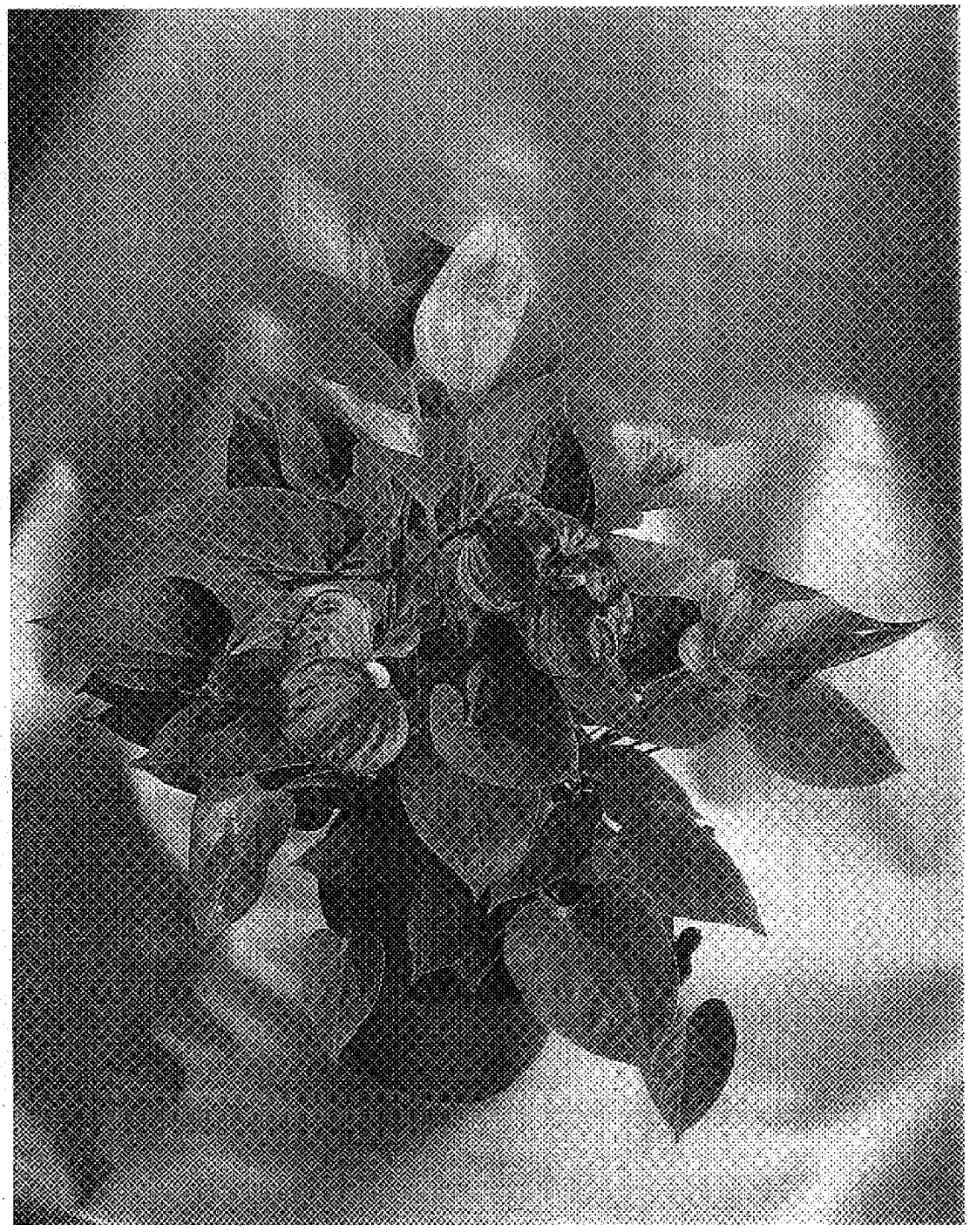

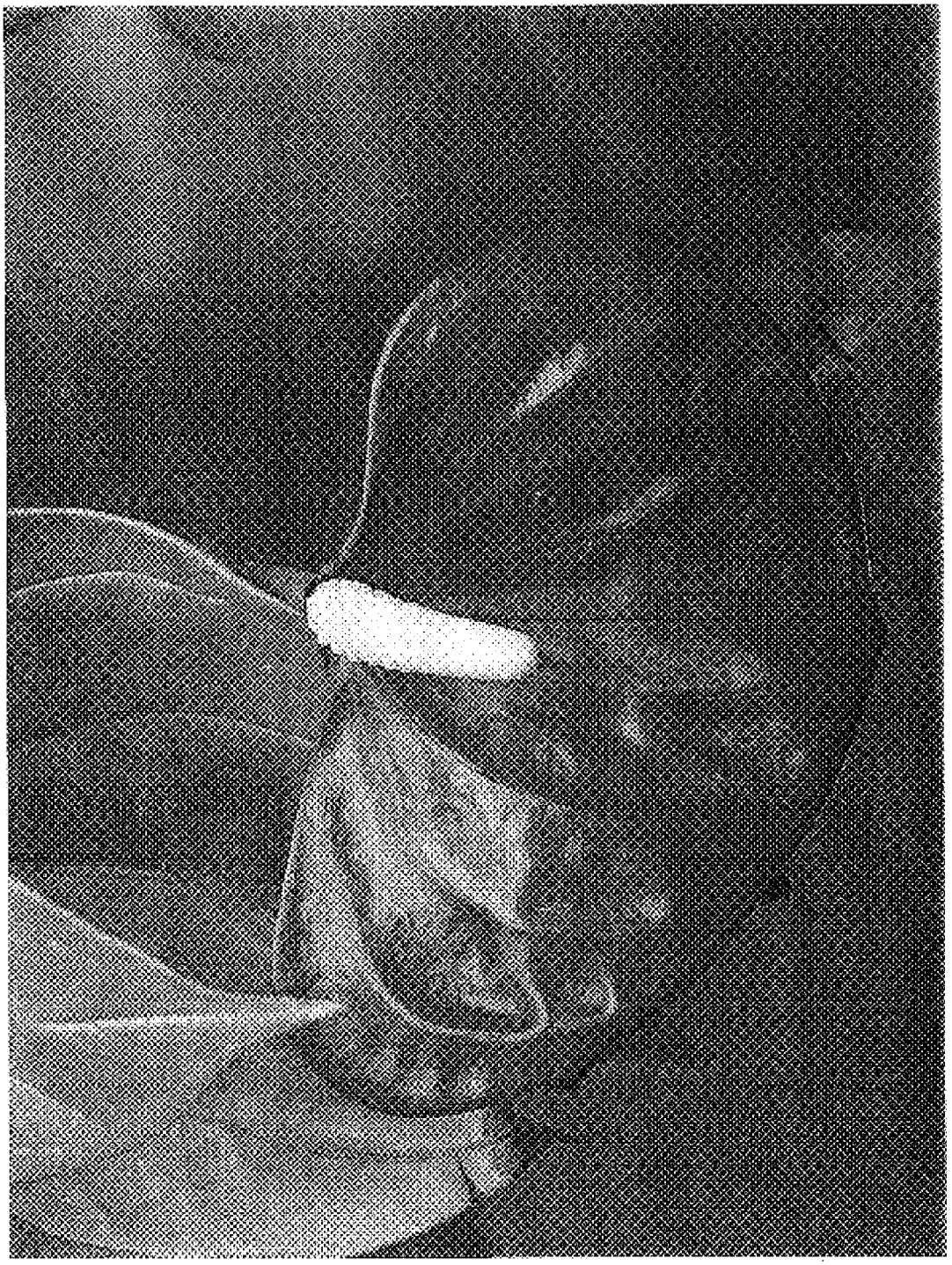

* * * * *